(12) United States Patent
Ebert et al.

(10) Patent No.: US 7,342,661 B2
(45) Date of Patent: Mar. 11, 2008

(54) METHOD FOR NOISE IMPROVEMENT IN ELLIPSOMETERS

(75) Inventors: Martin Ebert, Fremont, CA (US); Lanhua Wei, Fremont, CA (US)

(73) Assignee: Therma-Wave, Inc., Fremont, CA (US)

( * ) Notice: Subject to any disclaimer, the term of this patent is extended or adjusted under 35 U.S.C. 154(b) by 0 days.

(21) Appl. No.: 11/287,701

(22) Filed: Nov. 28, 2005

(65) Prior Publication Data

US 2006/0132773 A1    Jun. 22, 2006

Related U.S. Application Data

(60) Provisional application No. 60/633,070, filed on Dec. 3, 2004.

(51) Int. Cl.
*G01J 4/00* (2006.01)

(52) U.S. Cl. .................................................... 356/369

(58) Field of Classification Search ...................... None
See application file for complete search history.

(56) References Cited

U.S. PATENT DOCUMENTS

| | | | |
|---|---|---|---|
| 5,042,951 A | 8/1991 | Gold et al. | 356/369 |
| 5,181,080 A | 1/1993 | Fanton et al. | 356/632 |
| 5,412,473 A | 5/1995 | Rosencwaig et al. | 356/451 |
| 5,596,411 A | 1/1997 | Fanton et al. | 356/369 |
| 5,877,859 A | 3/1999 | Aspnes et al. | 356/364 |
| 5,973,787 A | 10/1999 | Aspnes et al. | 356/369 |
| 6,084,675 A | 7/2000 | Herzinger et al. | 356/369 |
| 6,134,012 A | 10/2000 | Aspnes et al. | 356/369 |
| 6,320,657 B1 | 11/2001 | Aspnes et al. | 356/369 |
| 6,353,477 B1 | 3/2002 | Johs et al. | 356/369 |
| 6,413,659 B1 * | 7/2002 | Rothberg | 428/822 |
| 6,449,043 B2 | 9/2002 | Aspnes et al. | 356/369 |
| 6,483,585 B1 * | 11/2002 | Yang | 356/369 |
| 6,650,415 B2 | 11/2003 | Aspnes et al. | 356/369 |
| 6,836,328 B2 | 12/2004 | Opsal | 356/369 |

* cited by examiner

*Primary Examiner*—Tu T. Nguyen
(74) *Attorney, Agent, or Firm*—Stallman & Pollock LLP

(57) ABSTRACT

A normalization procedure for an ellipsometric system having a rotating optical element such as a polarizer or compensator is disclosed. In operation, a first DC component is extracted from the measured output signals obtained during the first 180 degrees of rotation of the optical element and a second DC component is extracted from the output signals obtained during the second 180 degrees of rotation of the optical element. The first DC component is used to normalize the output signals obtained during the first 180 degrees of rotation of the optical element and the second DC component is used to normalize the output signals obtained during the second 180 degrees of rotation of the optical element.

10 Claims, 4 Drawing Sheets

US 7,342,661 B2

METHOD FOR NOISE IMPROVEMENT IN ELLIPSOMETERS

PRIORITY CLAIM

This application claims the benefit of U.S. Provisional Application No. 60/633,070, filed Dec. 3, 2004, which is incorporated herein by reference.

TECHNICAL FIELD

The subject invention relates to an optical metrology tool for inspecting and evaluating semiconductor wafers. This invention is particularly suited for measurements of samples using ellipsometers with rotating components, particularly broadband rotating compensator spectroscopic ellipsometers (RCSE).

BACKGROUND

There is considerable interest in monitoring properties of semiconductors at various stages during the fabrication process. Monitoring the properties during fabrication allows the manufacturer to detect and correct technological process problems prior to the completion of the wafer.

Inspection of actual product wafers during or between technological process steps usually require non-contact techniques. Accordingly, a number of tools have been developed for optically inspecting semiconductor wafers. Such tools include reflectometers and ellipsometers. To increase the robustness of the measurements, these tools can often obtain measurements at multiple wavelengths and/or multiple angles of incidence.

Therma-Wave, Inc., the assignee of the subject invention has developed a number of such tools over the last fifteen years. One of the first such tools is described in U.S. Pat. No. 4,999,014. In this tool, a probe beam from a laser is tightly focused on the sample with a high numerical aperture lens to create light rays with a spread of angles of incidence. The reflected beam is imaged onto an array detector. The location of the elements on the array detector can be mapped to different angles of incidence on the sample. This configuration is still in commercial use today in Therma-Wave's Opti-Probe® product line and is referred to as Beam Profile Reflectometry® or BPR®.

This concept was subsequently extended to ellipsometric measurement as described in U.S. Pat. No. 5,042,951. In this approach, the change in polarization state of the probe beam is monitored at multiple angles of incidence. Various polarizers and a waveplate (or compensator) are used to permit the polarization analysis. A variant of this approach which integrates the angular information is disclosed in U.S. Pat. No. 5,181,080. This configuration is also in commercial use and is referred to as Beam Profile Ellipsometry® or BPE®.

While the latter patents were directed primarily to single wavelength systems, efforts have been made to extend these concepts to multiple wavelength systems. See for example, U.S. Pat. Nos. 5,412,473 and 5,596,411.

The assignee herein has also made efforts to improve broadband spectroscopic ellipsometry. More specifically, and as described in U.S. Pat. Nos. 5,877,859, 5,973,787; 6,134,012; 6,320,657; 6,449,043, and 6,650,415, an improved spectroscopic ellipsometer system was proposed that utilized a rotating compensator (waveplate). Prior to these disclosures, rotating compensators were typically used only in narrow band ellipsometers, while rotating polarizers were used in broadband, spectroscopic ellipsometers. The above-mentioned patents disclose how a rotating compensator can be used in BPR and BPE type systems.

In an ideal ellipsometer having a rotating element (i.e., compensator), the DC component remains constant during the entire measurement. However, in all practical applications of ellipsometers, the DC component will change over time at different angular positions of the rotating element creating noise and decreasing accuracy of ellipsometric measurements.

Signal normalization to the DC component is one of the techniques known to improve accuracy and precision in ellipsometric measurements. Examples of DC normalization in rotating element spectroscopic ellipsometer systems can be found in U.S. Pat. Nos. 6,084,675 and 6,353,477. In these patents, the DC normalization is performed for the ellipsometric signal obtained during a full revolution of the rotating element. More specifically, the DC component is computed based on a full revolution of the rotating element and the Fourier coefficients are normalized against this DC component. While this approach improves the analysis, further improvements are desirable. All of the patent cited in the background section are incorporated herein by reference.

SUMMARY OF THE INVENTION

The subject invention proposes a normalization procedure for an ellipsometric system based on the calculation of DC component of the signal twice per rotation of the rotating optical element (e.g., polarizer or waveplate (compensator)). More specifically, a first DC component is extracted from the measured output signals obtained during the first 180 degrees of rotation of the optical element and a second DC component is extracted from the output signals obtained during the second 180 degrees of rotation of the optical element. The first DC component is used to normalize the output signals obtained during the first 180 degrees of rotation of the optical element and the second DC component is used to normalize the output signals obtained during the second 180 degrees of rotation of the optical element. In this manner, the subject invention increases the normalization frequency by a factor of two to help isolate the signals of interest from DC fluctuations.

Basic features of the subject invention will be discussed in conjunction with the continuously rotating compensator spectroscopic ellipsometry system. However, the same approach is applicable to ellipsometric systems of all other types: rotating analyzer/polarizer and single wavelength ellipsometric systems.

One of the significant advantages of a continuously rotating waveplate in an ellipsometer compared to a stepping waveplate, is the ability to normalize the $2^{nd}$ and $4^{th}$ harmonic components of the signal to the DC signal calculated from the signal collected during each rotation. The advantage is that this allows normalizing the signal against environmental noise at a higher frequency than it is possible for a stepping waveplate. However, the concepts disclosed herein could be used to improve measurements associated with a stepping waveplate.

Further objects and advantages of the subject invention will become apparent by a review of the specification, claims and appended figures.

DETAILED DESCRIPTION OF THE PREFERRED EMBODIMENT

Figure 4:
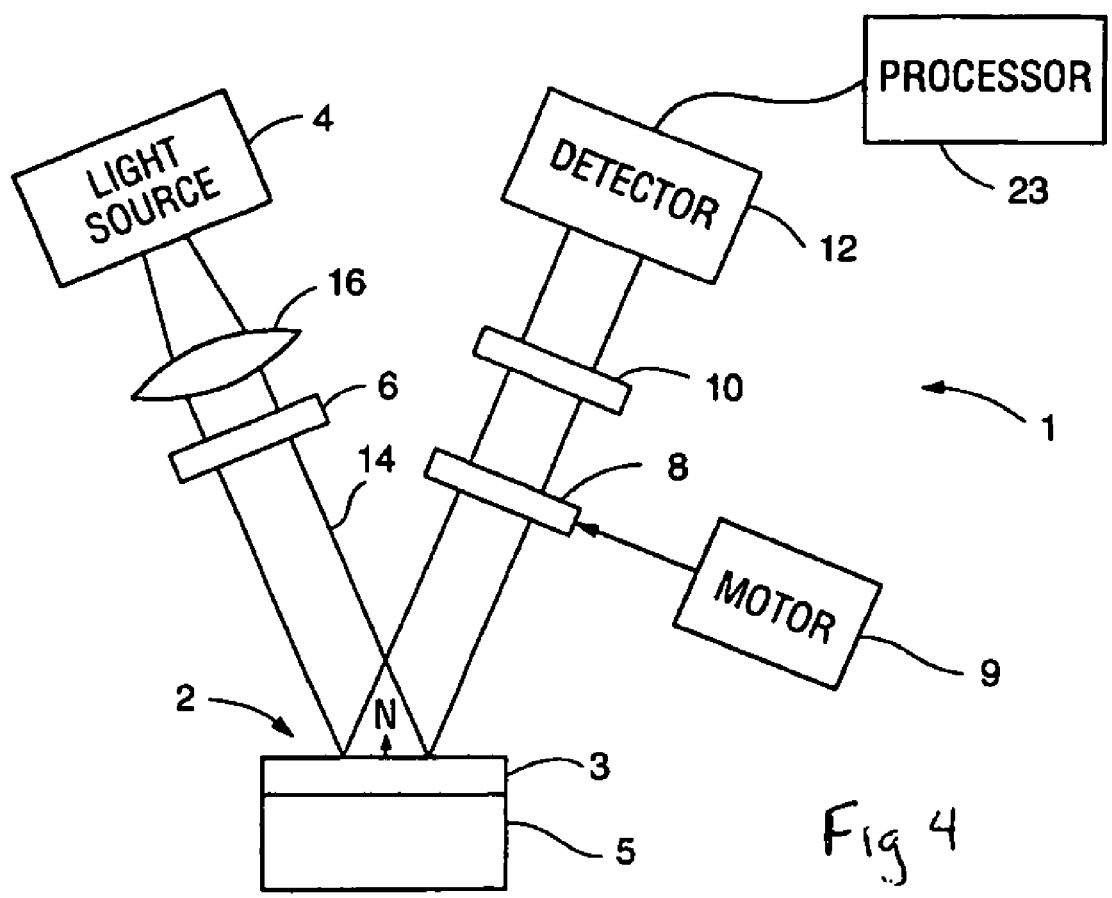
FIG. 4 is a schematic diagram of a spectroscopic ellipsometer with a rotating waveplate.

The subject invention has applicability to any ellipsometer operating with a rotating optical element, including polarizers and retarders (compensators). FIG. 4 illustrates one type of ellipsometer 1. Ellipsometer 1 is a spectroscopic ellipsometer with a rotating compensator of the type described in U.S. Pat. Nos. 5,877,859 and 6,278,519 both of which are incorporated by reference.

The ellipsometer for probing a sample 2 includes a broadband light source 4, a polarizer 6, a rotating compensator 8, an analyzer 10 and a detector 12. The light source 4 is a broadband light source that produces a spectrum of polychromatic light over a predetermined wavelength range of interest. The diverging probe beam 14 from the light source 4 is collimated by a lens 16. The beam 14 interacts with polarizer 6 to create a known polarization state. The azimuth angle of polarizer 6 is oriented so that the plane of the electric vector associated with the linearly polarized beam exiting from the polarizer 6 is at a known angle with respect to the plane of incidence (defined by the propagation direction of the beam 14 and the normal N to the exposed surface of the sample 2). The azimuth angle is preferably selected to be on the order of 30 degrees because the sensitivity is optimized when the reflected intensities of the P and S polarized components are approximately balanced. It should be noted that polarizer 6 can be omitted if a particular light source is used that emits light with the desired known polarization state The beam 14 is incident on, and reflects from, sample 2 at an oblique angle. In this illustration, sample 2 consists of a thin layer 3 formed on a substrate 5. Typically, the sample will consist of multiple layers and/or small geometric features (critical dimensions) which must be analyzed. The beam 14 is ideally incident on sample 2 at an angle on the order of 70 degrees to the normal N of the surface of the sample because sensitivity to sample properties is maximized in the vicinity of the Brewster or pseudo-Brewster angle of a material. Based upon well-known ellipsometric principles, the reflected beam will generally have a mixed linear and circular polarization state after interacting with the sample, as compared to the linear polarization state of the incoming beam.

The beam 14 then passes through the rotating compensator 8, which introduces a relative phase delay Δ (phase retardation) between a pair of mutually orthogonal polarized optical beam components. The amount of phase retardation is a function of the wavelength, the dispersion characteristics of the material used to form the compensator, and the thickness of the compensator. Compensator 8 is rotated at an angular velocity ω about an axis substantially parallel to the propagation direction of beam 14, preferably by an electric motor 9. Compensator 8 can be any conventional wave-plate compensator, for example those made of crystal quartz. The thickness and material of the compensator 8 is selected such that a desired range of phase retardations of the beam is induced by the range of wavelengths used to probe the sample.

Beam 14 then interacts with analyzer 10, which serves to mix the polarization states incident on it. In this embodiment, analyzer 10 is another linear polarizer, preferably oriented at an azimuth angle of 45 degrees relative to the plane of incidence. However, any optical device that serves to appropriately mix the incoming polarization states can be used as an analyzer. The analyzer 10 is preferably a quartz Rochon or Wollaston prism. The rotating compensator changes the polarization state of the beam as it rotates. By measuring the light transmitted by analyzer 10, the polarization state of beam 14 reflected from the sample can be determined.

Figure 1:
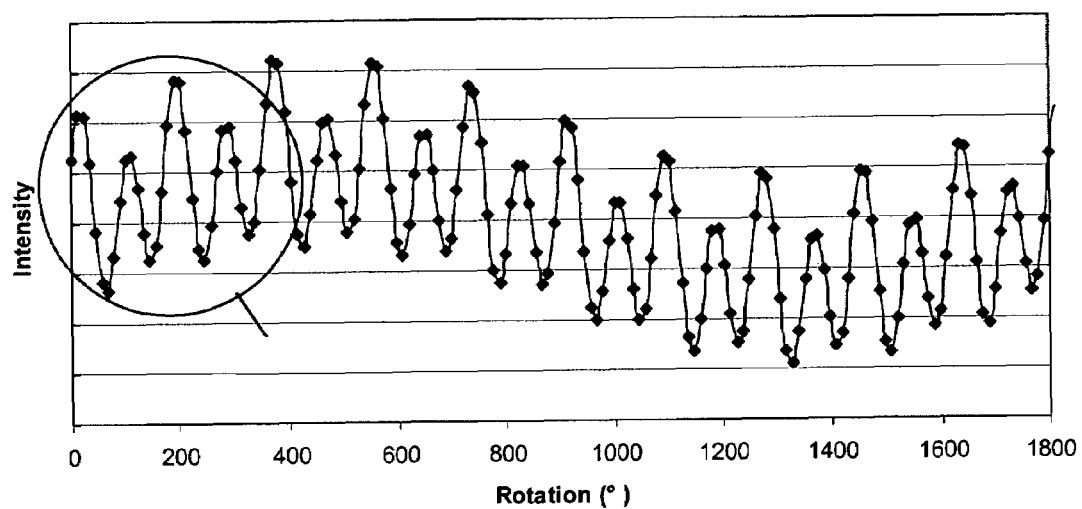
FIG. 1 is a plot of the varying intensity that would be obtained from an ellipsometer which included a rotating waveplate in the presence of a low frequency drift. Data is shown for five revolutions of the waveplate.

It should be noted that the compensator 8 can be located either between the sample 2 and the analyzer 10 (as shown in FIG. 1), or between the sample 2 and the polarizer 6.

Beam 14 then enters detector 12, which measures the intensity of the different wavelengths of light throughout the wavelength range of interest that pass through the compensator/analyzer combination. Detector 12 ideally includes a dispersive element such as a diffraction grating, prism or holographic plate, to angularly disperse the beam 14 as a function of wavelength to individual detector elements contained in a detector array. The different detector elements measure the optical intensities of the different wavelengths of light throughout the wavelength range of interest, preferably simultaneously. Alternately, the detector 12 can be a CCD camera, or a photomultiplier with suitably dispersive or otherwise wavelength selective optics. It should be noted that it is within the scope of this invention to use a monochrometer, etc., and measure the different wavelengths serially (one wavelength at a time) using a single detector element.

A processor 23 processes the intensity information measured by the detector 12 to determine the polarization state of the light after interacting with the analyzer, and the ellipsometric parameters of the sample. This information processing not only includes measuring beam intensity as a function of wavelength, but also measuring beam intensity as a function of the azimuth (rotational) angle of the compensator about its axis of rotation (which is substantially parallel to the propagation direction of beam 14). If the compensator is rotating continuously, this measurement of intensity as a function of compensator rotational angle is effectively a measurement of the intensity of beam 14 as a function of time, since the compensator angular velocity is usually known and a constant.

Figure 2:
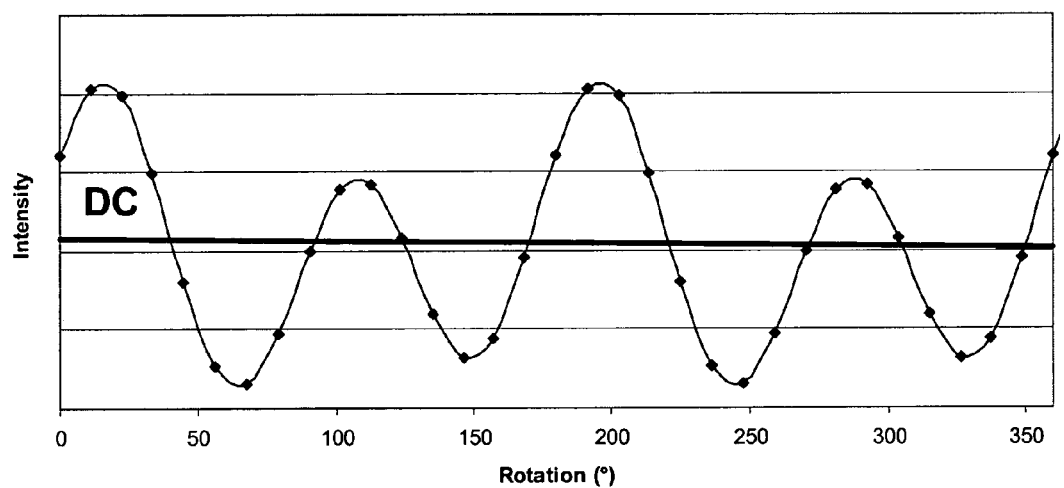
FIG. 2 is a plot of a portion of FIG. 1 showing the output from one revolution of the waveplate and illustrating the change in the DC component over the full revolution.

A typical output from an ellipsometer at one wavelength is shown in FIG. 1. As seen therein, the signal measured during one full rotation of the waveplate has both $2^{nd}$ and $4^{th}$ harmonic components. In this figure, a change in the intensity with a frequency that is slow compared to the rotation frequency can be superimposed to the signal. Such a change can result from drift in the optical and/or electronic components of the system, including variations in the light source output and the impact of environmental changes. In order to minimize the effect of such a changes in the signal, the Fourier coefficients calculated from these signals are usually normalized to the DC component of the signal taken during the full rotation of the waveplate as shown in FIG. 2.

Figure 3:
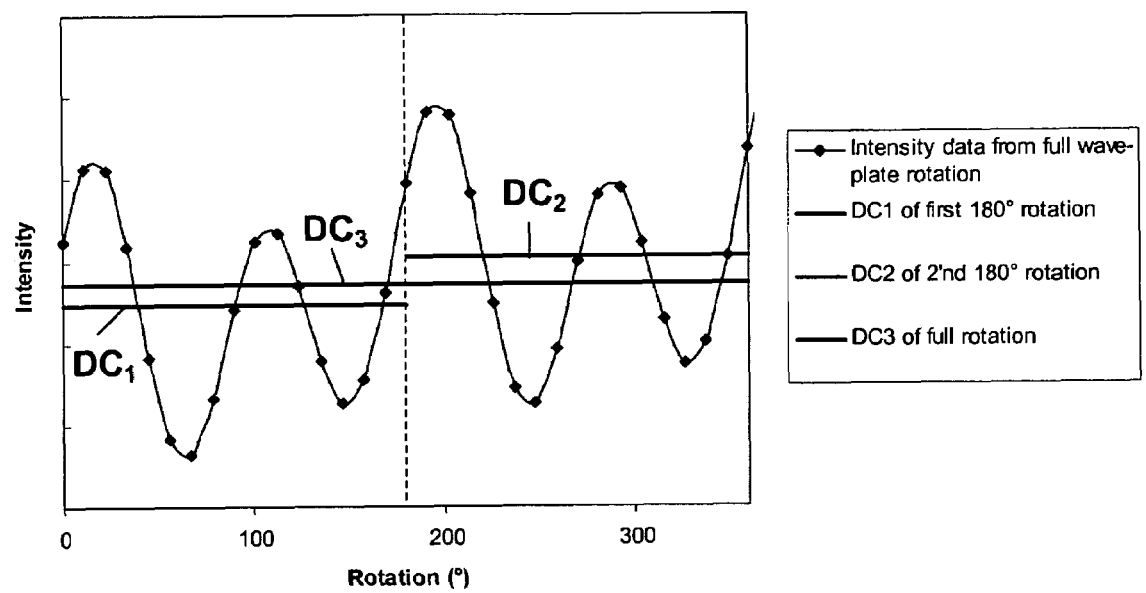
FIG. 3 is also a plot showing the output from one revolution of the waveplate and illustrating the change in two separate DC components, one over the first 180 degrees of rotation of the waveplate and the second over the second 180 degrees of rotation of the waveplate and comparing it to the DC component for a full rotation.

In FIG. 3 the effect of the subject invention is demonstrated. The same signal as shown in FIG. 2 is used, but the Fourier components are calculated for each half rotation (marked as $DC_1$, and $DC_2$). As a result, the Fourier coefficients can be normalized to a more accurate DC value (compared to that of the full rotation marked as $DC_3$), minimizing the effect of low frequency noise in the signal. In this approach, the data collected during one waveplate rotation is split into two sets of data. The processor calculates the $1^{st}$ and $2^{nd}$ harmonic of each data set (equivalent to the $2^{nd}$ and $4^{th}$ harmonic of a full rotation) and normalizes each set using the DC value calculated from each half rotation data set. This will increase the frequency of normalization and reduce the impact of environmental noise.

To be more specific, in the rotating compensator ellipsometer system discussed above, the signal S measured during a full rotation of the waveplate can be expressed as:

$$S=DC+C_2*\cos 2\omega+S_2*\sin 2\omega+C_4*\cos 4\omega+S_4*\sin 4\omega$$

where $\omega$ is the angular frequency of the waveplate full rotation and DC, $C_2$, $S_2$, $C_4$, $S_4$ are the Fourier coefficients of the $2^{nd}$ and $4^{th}$ harmonics, which carry the fundamental information about the optical system. In prior practice, the DC-normalized Fourier coefficients $C_2/DC$, $S_2/DC$, $C_4/DC$ and $S_4/DC$ are used to extract this information.

In the proposed scheme, the same signal is processed separately within each of the $1^{st}$ half rotation and $2^{nd}$ half rotation:

$$S_1=DC_1+C_{11}*\cos \omega'+S_{11}*\sin \omega'+C_{21}*\cos 2\omega'+S_{21}*\sin 2\omega'$$

$$S_2=DC_2+C_{12}*\cos \omega'+S_{12}*\sin \omega'+C_{22}*\cos 2\omega'+S_{22}*\sin 2\omega'$$

where $\omega'=2\omega$ is the angular frequency of the waveplate half rotation, and $DC_1$, $C_{11}$, $S_{11}$, $C_{21}$, $S_{21}$ are the Fourier coefficients of the $1^{st}$ and $2^{nd}$ harmonics of the 1St half rotation, while $DC_2$, $C_{12}$, $S_{12}$, $C_{22}$, $S_{22}$ are the Fourier coefficients of the $1^{st}$ and $2^{nd}$ harmonics of the $2^{nd}$ half rotation. Consequently, the DC-normalized Fourier coefficients are $C_{11}/DC_1$, $S_{11}/DC_1$, $C_{21}/DC_1$, and $S_{21}/DC_1$ and $C_{12}/DC_2$, $S_{12}/DC_2$, $C_{22}/DC_2$ and $S_{22}/DC_2$. As explained in the previous section, by taking advantage of faster $\omega'$(twice as fast as $\omega$), these half-period DC-normalized Fourier components are more immune to the low frequency noise which predominantly comes from the source or environment, and therefore provide more accurate results.

While the subject invention has been described in relation to a off-axis spectroscopic ellipsometer with a continuously rotating compensator it is believed to be useful in any ellipsometer that relies on a rotating optical element which modifies the polarization of the beam. This would include both broadband and single wavelength systems including broadband systems using a monochrometer. It would include typically off-axis systems as well as normal incidence systems as discussed in the above cited patents. Further it would include systems which relied on either a rotating polarizer or rotating analyzer. Finally, it would also include systems with pairs of rotating elements.

The subject invention could be used with simultaneously multiple angle of incidence ellipsometers of the type described in the above cited patents as well as: U.S. Pat. No. 6,836,328 and U.S. patent application, Ser. No. 11/269,204, filed Nov. 8, 2005, based on Provisional Application Ser. No. 60/627,824, filed Nov. 15, 2004, all of which are incorporated herein by reference.

It should be noted that in a rotating polarizer or analyzer system, a full rotation provides a two omega signal and does not include a four omega signal as with a rotating compensator system. Data taken over a half rotation of a polarizer system will include only a one omega signal and only the Fourier coefficients of the $1^{st}$ harmonics would be available.

What is claimed is:

1. An ellipsometer for evaluating a sample comprising:
    a light source for generating a probe beam which is directed to interact with the sample;
    a detector for measuring the intensity of the probe beam after interaction with the sample and generating output signals in response thereto;
    an optical element located in the path of the probe beam and being one of a polarizer or a retarder, said optical element being rotatable through 360 degrees about the propagation axis of the probe beam; and
    a processor for analyzing the output signals as a function of the rotational position of the optical element, said processor for extracting a first DC component from the output signals obtained during the first 180 degrees of rotation of the optical element and a second DC component from the output signals obtained during the second 180 degrees of rotation of the optical element, said processor using the first DC component to normalize the output signals obtained during the first 180 degrees of rotation of the optical element and using the second DC component to normalize the output signals obtained during the second 180 degrees of rotation of the optical element.

2. An ellipsometer as recited in claim 1, wherein the light source is a broadband light source and the rotating optical element is a compensator.

3. An ellipsometer as recited in claim 2, wherein the detector measures the intensity of the probe beam at a plurality of wavelengths simultaneously.

4. An ellipsometer as recited in claim 1, further including a motor for continuously rotating the optical element.

5. An ellipsometer for evaluating a sample comprising:
    a light source for generating a probe beam which is directed to interact with the sample;
    a detector for measuring the intensity of the probe beam after interaction with the sample and generating output signals in response thereto;
    a compensator located in the path of the probe beam, said compensator being continuously rotatable through 360 degrees about the propagation axis of the probe beam; and
    a processor for analyzing the output signals as a function of the rotational position of the compensator, said processor for extracting a first DC component from the output signals obtained during the first 180 degrees of rotation of the compensator and a second DC component from the output signals obtained during the second 180 degrees of rotation of the compensator, said processor performing a Fourier analysis on the output signals to extract the first and second harmonic components for both the first and second 180 degrees of rotation and using the first DC component to normalize the first and second harmonic components of the output signals obtained during the first 180 degrees of rotation of the optical element and using the second DC component to normalize the first and second harmonic components of the output signals obtained during the second 180 degrees of rotation of the optical element.

6. An ellipsometer as recited in claim 5, wherein the light source is a broadband light source.

7. An ellipsometer as recited in claim 6, wherein the detector measures the intensity of the probe beam at a plurality of wavelengths simultaneously.

8. A method of normalizing the signals generated by a detector of an ellipsometer of the type that includes a rotating optical element selected from the group consisting of an analyzer and a compensator, said method comprising the steps of:

extracting a first DC component from the output signals obtained during the first 180 degrees of rotation of the compensator;

extracting a second DC component from the output signals obtained during the second 180 degrees of rotation of the compensator;

normalizing the output signals obtained during the first 180 degrees of rotation of the compensator using the first DC component;

normalizing the output signals obtained during the second 180 degrees of rotation of the compensator using the second DC component; and storing the results of both said normalizing steps.

9. A method as recited in claim 8, wherein said optical element is continuously rotating.

10. A method of normalizing the signals generated by a detector of an ellipsometer of the type that includes a continuously rotating compensator, said method comprising the steps of:

extracting a first DC component from the output signals obtained during the first 180 degrees of rotation of the compensator;

extracting a second DC component from the output signals obtained during the second 180 degrees of rotation of the compensator;

computing first Fourier coefficients of the first and second harmonics of the output signals obtained during the first 180 degrees of rotation of the compensator and using the first DC component to normalize said first coefficients; and computing second Fourier coefficients of the first and second harmonics of the output signals obtained during the second 180 degrees of rotation of the compensator and using the second DC component to normalize said second coefficients; and storing the results of both said computing steps.

* * * * *